US007585827B2

(12) United States Patent  
Geary et al.

(10) Patent No.: US 7,585,827 B2
(45) Date of Patent: Sep. 8, 2009

(54) CONDITIONING SHAMPOO COMPOSITIONS CONTAINING A MIXTURE OF SELECT CATIONIC CONDITIONING POLYMERS

(75) Inventors: Nicholas William Geary, Blue Ash, OH (US); Kendrick Jon Hughes, Cincinnati, OH (US); Mark Anthony Brown, Union, KY (US); Timothy Woodrow Coffindaffer, Maineville, OH (US); Afua Asiedua Asante, Cincinnati, OH (US); Robert Lee Wells, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/894,144

(22) Filed: Aug. 20, 2007

(65) Prior Publication Data

US 2007/0289613 A1 Dec. 20, 2007

Related U.S. Application Data

(63) Continuation of application No. 10/454,234, filed on Jun. 4, 2003, now abandoned.

(60) Provisional application No. 60/385,794, filed on Jun. 4, 2002.

(51) Int. Cl.
C11D 3/37 (2006.01)
(52) U.S. Cl. .................. 510/119; 510/123; 510/130; 510/237; 510/264; 510/504
(58) Field of Classification Search ............ 510/119, 510/123, 130, 237, 264, 504
See application file for complete search history.

(56) References Cited

U.S. PATENT DOCUMENTS

| 2,396,278 | A | 3/1946 | Lind |
| 2,438,091 | A | 3/1948 | Lynch |
| 2,486,921 | A | 11/1949 | Byerly |
| 2,486,922 | A | 11/1949 | Strain |
| 2,528,378 | A | 10/1950 | Mannheimer |
| 2,658,072 | A | 11/1953 | Milton |
| 2,694,668 | A | 11/1954 | Fricke |
| 2,809,971 | A | 10/1957 | Bernstein |
| 2,826,551 | A | 11/1958 | Geen |
| 3,152,046 | A | 10/1964 | Ales |
| 3,236,733 | A | 2/1966 | Karsten |
| 3,332,880 | A | 7/1967 | Kessler |
| 3,753,196 | A | 8/1973 | Kurtz |
| 3,761,418 | A | 9/1973 | Parran |
| 3,929,678 | A | 12/1975 | Laughlin |
| 3,964,500 | A | 6/1976 | Drakoff |
| 4,089,945 | A | 5/1978 | Brinkman |
| 4,152,416 | A | 5/1979 | Spitzer |
| 4,197,865 | A | 4/1980 | Jacquet |
| 4,217,914 | A | 8/1980 | Jacquet |
| 4,299,817 | A | 11/1981 | Hannan, III et al. |
| 4,323,683 | A | 4/1982 | Bolich, Jr. |
| 4,364,837 | A | 12/1982 | Pader |
| 4,470,982 | A | 9/1984 | Winkler |
| 4,507,280 | A | 3/1985 | Pohl |
| 4,529,586 | A | 7/1985 | De Marco |
| 4,534,964 | A * | 8/1985 | Herstein et al. ............. 510/124 |
| 4,741,855 | A | 5/1988 | Grote |
| 4,885,107 | A | 12/1989 | Wetzel |
| 5,037,818 | A | 8/1991 | Sime |
| 5,104,646 | A | 4/1992 | Bolich, Jr. |
| 5,106,609 | A | 4/1992 | Bolich, Jr. |
| 5,409,628 | A | 4/1995 | Heinz |
| 5,543,074 | A * | 8/1996 | Hague et al. ................ 510/122 |
| 5,556,628 | A | 9/1996 | Derian |
| 5,573,709 | A | 11/1996 | Wells |
| 5,580,494 | A | 12/1996 | Sandhu |
| 5,624,666 | A | 4/1997 | Coffindaffer |
| 5,661,118 | A | 8/1997 | Cauwet |
| 5,674,478 | A | 10/1997 | Dodd |
| 5,716,605 | A | 2/1998 | Onitsuka |
| 5,750,122 | A | 5/1998 | Evans |

(Continued)

FOREIGN PATENT DOCUMENTS

EP 231997 A2 1/1987

(Continued)

OTHER PUBLICATIONS

PCT Search Report dated Oct. 22, 2003, 6 pages.

Primary Examiner—Charles I Boyer
(74) Attorney, Agent, or Firm—Laura R. Grunzinger; Idris N. McKelvey

(57) ABSTRACT

Disclosed are aqueous conditioning shampoo compositions which comprise an anionic detersive surfactant component; from about 0.025% to about 5% by weight of an water soluble or dispersible, cationic, non crosslinked, deposition or conditioning polymer; the conditioning shampoo may additionally comprise dispersed, liquid, droplets of a water insoluble, hair conditioning agent having a volume average particle diameter of from about 5 microns to about 125 microns. A homopolymer has a cationic charge density from about from about 2 meq/gm to about 4 meq/gm or a cationic charge density of from about 5 meq/gm to about 10 meq/gm; or an average molecular weight of at least 500,000. A copolymer is formed from one or more cationic monomer units and one or more nonionic monomer units or monomer units bearing a negative charge wherein the subsequent charge of the copolymer is positive. The cationic polymer, in combination with anionic detersive surfactant component and other essential components, provides improved deposition of the conditioning agent on hair or skin, even when the dispersed conditioning agent particles have a volume average particle size of up to about 125 microns. The composition may be applied to skin or hair, and provides improved conditioning performance even without the use of the dispersed hair conditioning agent particles.

9 Claims, No Drawings

U.S. PATENT DOCUMENTS

| | | | |
|---|---|---|---|
| 5,756,436 | A | 5/1998 | Royce |
| 5,776,871 | A | 7/1998 | Cothran |
| 5,804,207 | A | 9/1998 | Dubief |
| 5,811,087 | A | 9/1998 | Mohring |
| 5,863,526 | A | 1/1999 | Yeung |
| 5,874,073 | A * | 2/1999 | Kaiser et al. ............. 424/70.11 |
| 5,876,705 | A | 3/1999 | Uchiyama |
| 5,932,202 | A | 8/1999 | Guskey |
| 5,932,203 | A | 8/1999 | Coffindaffer |
| 5,935,561 | A | 8/1999 | Inman |
| 5,977,036 | A | 11/1999 | Guskey |
| 5,977,038 | A | 11/1999 | Birtwistle |
| 6,004,544 | A | 12/1999 | Schrader |
| 6,036,965 | A | 3/2000 | Gubernick |
| 6,040,282 | A | 3/2000 | Guskey |
| 6,057,275 | A * | 5/2000 | Fair et al. ................... 510/151 |
| 6,074,633 | A | 6/2000 | Dubief |
| 6,087,322 | A | 7/2000 | Morelli |
| 6,090,773 | A | 7/2000 | Lukenbach |
| 6,110,451 | A * | 8/2000 | Matz et al. ............... 424/70.16 |
| 6,180,576 | B1 | 1/2001 | Melby |
| 6,248,317 | B1 | 6/2001 | Snyder |
| 6,335,000 | B1 * | 1/2002 | Pratley ........................ 424/47 |
| 6,355,231 | B1 * | 3/2002 | Dieing et al. ............... 424/70.1 |
| 6,602,836 | B2 * | 8/2003 | Chiou et al. ................. 510/220 |
| 6,608,011 | B2 | 8/2003 | Patel |
| 6,627,184 | B2 | 9/2003 | Coffindaffer |
| 6,849,584 | B2 * | 2/2005 | Geary et al. ................. 510/119 |
| 6,930,078 | B2 | 8/2005 | Wells |
| 6,939,536 | B2 * | 9/2005 | Chen et al. ................. 424/70.1 |
| 2001/0005932 | A1 | 7/2001 | Itoh |
| 2003/0091521 | A1 | 5/2003 | Midha |
| 2003/0091524 | A1 | 5/2003 | Yang |
| 2003/0138392 | A1 | 7/2003 | Royce |
| 2003/0223951 | A1 | 12/2003 | Geary |
| 2004/0157754 | A1 | 8/2004 | Geary |
| 2004/0235702 | A1 | 11/2004 | Hawkins |
| 2005/0028293 | A1 * | 2/2005 | Geffroy ..................... 8/115.51 |

FOREIGN PATENT DOCUMENTS

| | | |
|---|---|---|
| EP | 661962 A1 | 9/1993 |
| GB | 849433 A | 8/1957 |
| WO | WO1997026854 A1 | 1/1997 |
| WO | WO1997029736 A1 | 1/1997 |
| WO | WO1998018434 A1 | 10/1997 |
| WO | WO1993008787 A2 | 10/1999 |

* cited by examiner

CONDITIONING SHAMPOO COMPOSITIONS CONTAINING A MIXTURE OF SELECT CATIONIC CONDITIONING POLYMERS

CROSS REFERENCE TO RELATED APPLICATION

The application is a continuation of U.S. patent application Ser. No. 10/454,234 filed Jun. 4, 2003 now abandoned which claims the benefit of U.S. Provisional application Ser. No. 60/385,794, filed on Jun. 4, 2002.

FIELD OF THE INVENTION

The present invention relates to conditioning shampoo compositions with improved conditioning performance which comprise select cationic deposition polymers.

BACKGROUND OF THE INVENTION

Conditioning shampoos comprising various combinations of detersive surfactant and hair conditioning agents are known. These shampoo products typically comprise an anionic detersive surfactant in combination with a conditioning agent such as silicone, hydrocarbon oil, fatty esters, or combinations thereof. These shampoos have become more popular among consumers as a means of conveniently obtaining hair conditioning and hair cleansing performance all from a single hair care product.

Many conditioning shampoos, however, do not provide sufficient deposition of conditioning agents onto hair during the shampooing process. Without such deposition, large proportions of conditioning agent are rinsed away during the shampooing process and therefore provide little or no conditioning benefit. Without sufficient deposition of the conditioning agent on the hair, relatively high levels of conditioning agents may be needed in the shampoo composition to provide adequate hair conditioning performance. Such high levels of a conditioning agent, however, can increase raw material costs, reduce lathering, and present product stability concerns.

Obtaining good deposition of a conditioning agent onto hair is further complicated by the action of detersive surfactants in the shampoo. Detersive surfactants are designed to carry away or remove, oil, grease, dirt, and particulate matter from the hair and scalp. In doing so, the detersive surfactants can also interfere with deposition of the conditioning agent, and carry away both deposited and non deposited conditioning agent during rinsing. This further reduces deposition of the conditioning agent onto the hair after rinsing, thus further reducing hair conditioning performance.

One known method for improving deposition of a hair conditioning agent onto hair involves the use of certain cationic deposition polymers. These polymers may be synthetic, but are most typically natural cellulosic or guar polymers that have been modified with cationic substituents. The cationic charge density of such polymers, especially when used in a shampoo composition, is minimized so as to avoid incompatibility with anionic materials in the shampoo such as anionic surfactant. As such, most shampoos which contain both an anionic detersive surfactant and a cationic deposition polymer will maintain relatively low cationic charge density values for the deposition polymer in order to maintain physical stability of the shampoo composition.

A need still exists for improved conditioning performance in shampoo compositions.

SUMMARY OF THE INVENTION

The present invention is directed to conditioning shampoo compositions which comprise:
(A) from about 5% to about 50% by weight of a detersive surfactant component selected from the group consisting of anionic surfactants, amphoteric or zwitterionic surfactants having an attached group that is anionic at the pH of the composition, and combinations thereof;
(B) from about 0.025% to about 5% by weight of an water soluble or dispersible, cationic, non crosslinked, conditioning polymer having one or more of the following characteristics:
   i. a cationic charge density of from about 2 meq/gm to about 4 meq/gm or a cationic charge density of at least 5 meq/gm, and/or
   ii. an average molecular weight of at least 500,000, and/or
   iii. a copolymer formed from one or more cationic monomer units and one or more nonionic monomer units or monomer units bearing a terminal negative charge wherein the subsequent charge of the copolymer is positive; and
(C) from about 20% to about 94% by weight of water.

The present invention also relates to conditioning shampoo compositions which also contain from about 0.05% to 20% by weight of dispersed particles of a water insoluble, conditioning agent having a volume average particle diameter of from about 5 microns to about 125 microns. The select conditioning polymers defined herein, in combination with the other essential components, provide improved deposition of the conditioning agent on hair or skin.

DETAILED DESCRIPTION OF THE INVENTION

The shampoo compositions of the present invention can comprise, consist of, or consist essentially of the essential elements and limitations of the invention described herein, as well any of the additional or optional ingredients, components, or limitations described herein.

One embodiment of the present invention concerns the surprising discovery that compositions combining certain water soluble or dispersible, cationic, non crosslinked, deposition polymers in combination with surfactants form microscopically-phase separate lyotropic liquid crystals suspended in an aqueous surfactant phase. In use, the dispersed, concentrated polymer lyotropic liquid crystal phase provides improved hair and skin conditioning.

Moreover, without being limited to a particular theory, it appears that when dispersed conditioning agent particles are added to the matrix, the concentrated polymer lyotropic liquid crystal phase provides an improved mechanism for conditioning agent deposition, yielding conditioning agent deposition that results in more conditioning.

The liquid crystalline state exists between the boundaries of the solid crystalline phase and the isotropic liquid phase (i.e. an intermediate between the three dimensionally ordered crystalline state and the disordered dissolved state). In this state, some of the molecular order characteristics of the solid crystalline phase are retained in the liquid state because of the molecular structure and short range intermolecular interaction. The ability of some compounds to form a liquid crystalline mesophase had been observed nearly a century ago.

Liquid crystals are also known as anisotropic fluids, a fourth state of matter, polymer association structure or mesophases. Those terms are used interchangeably. Lyotropic means a material is formed through changes in solution behavior (and hence by definition contains a solvent, for example water) of the ingredients. The changes involve thermal and solvation energies. The term "lyotropic liquid crystal" as used herein, refers to a liquid crystalline phase distinctive by the presence of birefringence (a non-limiting example of which is formation of maltese crosses) under polarized light microscopy. These are most easily observed in the absence of particles as some particles also demonstrate birefringence. In addition, the term "polymer liquid crystals", as used herein, means "polymeric lyotropic liquid crystals" unless otherwise specified.

In general, liquid phases refer to the manner in which molecules, in this case cationic polymers and the anionic detersive surfactants, are arranged in space within a phase (this case involves a continuous aqueous phase). This phase is significantly more ordered than an ordinary liquid, but significantly less ordered than crystalline solids. If we consider a crystalline solid to have order in all directions, X, Y and Z then liquid crystals are phases that are ordered or crystalline in only one or two of their three possible orthogonal directions and are disordered (random or liquid-like) in the other dimensions. Cross-linked polymers have the back bones of the polymers chemically bound to each other. This forms a 3-dimensional polymer structure and without being bound by theory, the desired lytropic liquid crystal consist as layers of polymer and surfactant and hence the polymer needs a certain degree of flexibility to form the liquid crystal phase. The inflexibility of the cross-linked polymer is therefore not preferred. Reference: Chapter 8 "The Aqueous Phase Behavior of Surfactants" by R. G. Laughlin. Lamellar liquid crystals are ordered in only the Z direction perpendicular to the plane of the layers and disordered in the X & Y directions within the plane of the layers. Preferably, lamellar liquid crystals are formed in the cleansing composition of the present invention and incorporate non-crosslinked cationic polymers.

Liquid crystals are substances that possess mechanical properties resembling those of fluids, yet are capable of transmitting light when viewed with cross polars (birefringence) under static conditions. Some cases may show Bragg reflections characteristic of a well-defined molecular spacing. They have high degrees of orientational order and chain extensions.

The light microscopy of liquid crystals is described in The Microscopy of Liquid Crystals, Norman Hartshorne, Microscopy Publications, Ltd., Chicago, Ill., U.S.A., 1974. Birefringence occurs in general for mesomorphic states. Methods for microscopic observation and evaluation are discussed in Chapter 1, pp. 1-20, and in Chapter 6, pp. 79-90. A preferred method for determining occurrence of liquid crystals is by observing birefringence (a non-limiting example of which is formation of maltese crosses) of thin liquid crystal films between glass slides or from thin slices of a material under a polarizing microscope.

Liquid crystals are known to be used as thickeners in shampoo compositions. The formation of lamellar phase liquid crystals in surfactant systems is disclosed (in the context of thickening the product) in U.S. Pat. No. 5,556,628, WO2001005932 and EP796615.

It is also known to use polymers to form liquid crystalline phases for the sole purpose of thickening (often called thickening gels). EP 796614 teaches the use of polymers to thicken shampoos, but teach a class of polymers known to cross-link. Moreover, EP796614 teaches the use of inverse emulsion preparation of the polymer gel, which is a technique synonymous with cross-linked polymers.

A further embodiment of the present invention concerns the surprising discovery that particular types of polymeric liquid crystals yield improved conditioning, even without the presence of any additional conditioning agents. Without being limited by theory, these correspond to large and/or more viscous polymeric liquid crystals. The following table exemplifies several of the highly preferred polymers and their liquid crystal size and their Theological property as measured by the storage modulus G'.

The liquid crystal size was measured via standard polarized light microscopy and the size reported as a range based on a finite number of observations. The observed size depends greatly on the preparation technique (for example, the amount of shear in making the cleansing composition) and the following data were measured using a standardized making procedure. The rheological property G' is defined as the storage modulus and is the part of the shear stress that is in phase with the (shear) strain divided by the strain under sinusoidal conditions. The units of measure are Pa. Additional information may be obtained from "An Introduction to Rheology" by Barnes et al., Elsevier, 1998, incorporated herein by reference.

|  | MW | Polymeric Liquid Crystal size microns | G' of Polymeric liquid crystal |
| --- | --- | --- | --- |
| MAPTAC (0) | 220,000 | 5-7 | 500 |
| HMW MAPTAC (1) | 860,000 | 7-9 | 1000 |
| HHMW MAPTAC (2) | 1,500,000 | 8-10 | 1500 |
| Diquat (3) | 900,000 | 9-11 | 750 |

(0), (1), (2) 1-Propanaminium, N,N,N-trimethyl-3-[(2-methyl-1-oxo-2-propenyl)amino]-, chloride; (Poly(Methacrylamidopropyl trimethyl ammonium chloride))
(3) Methacryloamidopropyl-pentamethyl-1,3-propylene-2-ol-ammonium dichloride These data refer to homopolymers of the preferred synthetic cationic polymers, and clearly demonstrate that synthetic cationic polymers with higher molecular weight yield larger polymeric liquid crystals sizes and liquid crystals with higher values of G'.

The inventors have discovered that production of the preferred type of polymeric liquid crystal can be achieved through utilizing the polymers with the following characteristics:

a. a cationic charge density of from about 2 meq/gm to about 4 meq/gm or a cationic charge density of at least 5 meq/gm, or b. an average molecular weight of at least 500,000, or c. A copolymer formed from one or more cationic monomer units and one or more nonionic monomer units or monomer units bearing a terminal negative charge wherein the subsequent charge of the copolymer is positive.

A further objective of the present invention is to deposit efficacious levels of dispersed conditioning agent particles. U.S. Pat. No. 5,756,436 (Royce et al.) teaches the use of certain cationic deposition polymers for improved deposition of particles, dispersions and mixes thereof. The polymers taught herein all provide significant benefits (as demonstrated herein) and structurally differ from those taught by Royce et al. by at least one of the above criteria. Royce et al. teaches away from copolymers and teaches low molecular weights and different charge densities versus those taught herein. The use of such polymers is also taught by U.S. Pat. No. 5,661, 118, WO 9726860, EP 231997 and WO9729736; the latter requiring the use of zwitterionic and amphoteric surfactants—a restriction not required herein.

In one embodiment, the personal cleansing compositions of the present invention include surfactant, a cationic polymer and water. In another preferred embodiment the personal cleansing compositions of the present invention include surfactant, a cationic polymer, conditioning agent and water. Each of these components, as well as other preferred or optional components, are described in detail hereinafter.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified.

All molecular weights as used herein are weight average molecular weights expressed as grams/mole, unless otherwise specified.

The term "charge density", as used herein, refers to the ratio of the number of positive charges on a monomeric unit of which a polymer is comprised to the molecular weight of said monomeric unit. The charge density multiplied by the polymer molecular weight determines the number of positively charged sites on a given polymer chain.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

The term "fluid" as used herein, means a liquid or a gas which tends to take the shape of its container, container being the wall of the flexible hollow particles.

The term "lamellar liquid crystal" as used herein, means a material that is ordered in only the Z direction perpendicular to the plane of the layers and disordered in the X & Y directions within the plane of the layers.

The term "liquid crystal" as used herein, means a material having phases that are ordered and/or crystalline in only one or two of their three possible orthogonal directions and are disordered (random and/or liquid-like) in the other dimensions.

The term "lyotropic" as used herein, means a material is formed through changes in solution behavior of the ingredients. The changes involve thermal and solvation energies.

The term "phase separation" as used herein, means the formation of two thermodynamically stable liquid phases which exist, not as distinct bulk layers, but as a stable emulsion comprising droplets of one phase dispersed in another phase.

The term "polymer" as used herein shall include materials whether made by polymerization of one type of monomer or made by two (i.e., copolymers) or more types of monomers.

The term "suitable for application to human hair" as used herein, means that the compositions or components thereof so described are suitable for use in contact with human hair and the scalp and skin without undue toxicity, incompatibility, instability, allergic response, and the like.

The term "water soluble" as used herein, means that the polymer is soluble in water in the present composition. In general, the polymer should be soluble at 25° C. at a concentration of 0.1% by weight of the water solvent, preferably at 1%, more preferably at 5%, more preferably at 15%.

As used herein, "nonvolatile" refers to any material having little or no significant vapor pressure under ambient conditions, and a boiling point under one atmosphere (atm) preferably at least about 250° C. The vapor pressure under such conditions is preferably less than about 0.2 mm.

All cited references are incorporated herein by reference in their entireties. Citation of any reference is not an admission regarding any determination as to its availability as prior art to the claimed invention.

Detersive Surfactant Component

The shampoo compositions of the present invention comprise an anionic detersive surfactant component to provide cleaning performance to the composition. The anionic detersive surfactant component in turn comprises anionic detersive surfactant, zwitterionic or amphoteric detersive surfactant which has an attached group that is anionic at the pH of the composition, or a combination thereof, preferably anionic detersive surfactant. Such surfactants should be physically and chemically compatible with the essential components described herein, or should not otherwise unduly impair product stability, aesthetics or performance.

Suitable anionic detersive surfactant components for use in the shampoo composition herein include those which are known for use in hair care or other personal care cleansing compositions. The concentration of the anionic surfactant component in the shampoo composition should be sufficient to provide the desired cleaning and lather performance, and generally range from about 5% to about 50%, preferably from about 8% to about 30%, more preferably from about 10% to about 25%, even more preferably from about 12% to about 18%, by weight of the composition.

Preferred anionic surfactants suitable for use in the shampoo compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula $[R^1—SO_3\text{-}M]$ where $R^1$ is a straight or branched chain, saturated, aliphatic hydrocarbon radical having from about 8 to about 24, preferably about 10 to about 18, carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278, 3,332,880 and 5,756,436 (Royce et al.) which descriptions are incorporated herein by reference.

Preferred anionic detersive surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Suitable amphoteric or zwitterionic detersive surfactants for use in the shampoo composition herein include those which are known for use in hair care or other personal care cleansing composition, and which contain a group that is anionic at the pH of the shampoo composition. Concentration of such amphoteric detersive surfactants preferably ranges from about 0.5% to about 20%, preferably from about 1% to about 10%, by weight of the composition. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.), which descriptions are incorporated herein by reference.

Amphoteric detersive surfactants suitable for use in the shampoo composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate.

Zwitterionic detersive surfactants suitable for use in the shampoo composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The shampoo compositions of the present invention may further comprise additional surfactants for use in combination with the anionic detersive surfactant component described hereinbefore. Suitable optional surfactants include nonionic surfactants, cationic surfactants, and combinations thereof. Any such surfactant known in the art for use in hair or personal care products may be used, provided that the optional additional surfactant is also chemically and physically compatible with the essential components of the shampoo composition, or does not otherwise unduly impair product performance, aesthetics or stability. The concentration of the optional additional surfactants in the shampoo composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the shampoo compositions are described in *McCutcheon's, Emulsifiers and Detergents*, 1989 *Annual*, published by M. C. Publishing Co., and U.S. Pat. Nos. 3,929,678, 2,658,072; 2,438,091; 2,528,378, which descriptions are incorporated herein by reference.

Synthetic Cationic Polymer

The shampoo compositions of the present invention comprise certain cationic deposition or conditioning polymers that, in combination with the anionic surfactant component and other essential components herein, form polymeric liquid crystals. The polymers can be formulated in a stable shampoo composition that provides improved conditioning performance when formulated without additional conditioning actives, and also provides improved deposition of the conditioning agent particles (described herein) onto hair. The cationic synthetic polymer may be formed from
 i) one or more cationic monomer units, and optionally
 ii) one or more momomer units bearing a terminal negative charge, and/or
 iii) a functional nonionic momomer, wherein the subsequent charge of the copolymer is positive. The ratio of the three types of monomers is given by m, p and q where m is the number of cationic monomers, p the number of momomers bearing a terminal negative charge and q is the number of functional nonionic momomers.

The synthetic cationic polymers suitable for use in the shampoo composition herein are water soluble or dispersible, non crosslinked, cationic polymers having the following structure:

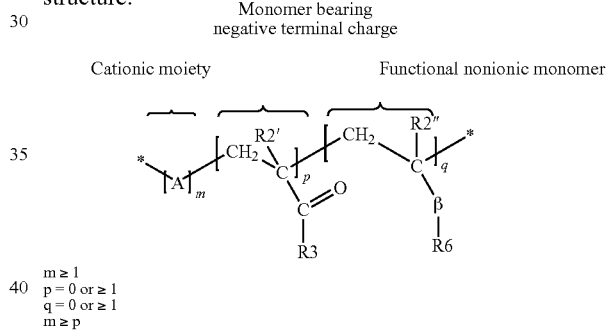

$m \geq 1$
$p = 0$ or $\geq 1$
$q = 0$ or $\geq 1$
$m \geq p$

Where A, may be one or more of the following cationic moieties:

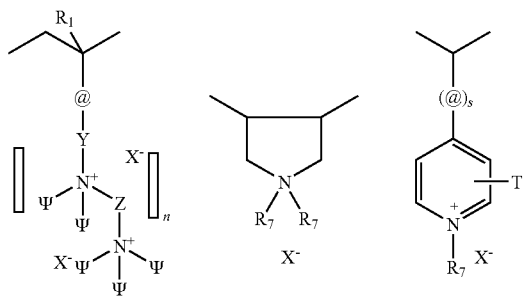

Where @=amido, alkylamido, ester, ether, alkyl or alkylaryl.

Where Y=C1-C22 alkyl, alkoxy, alkylidene, alkyl or aryloxy

Where ψ=C1-C22 alkyl, alkyloxy, alkyl aryl or alkyl aryloxy

Where Z=C1-C22 alkyl, alkyloxy, aryl or aryloxy

Where R1=H, C1-C4 linear or branched alkyl

Where s=0 or 1, n=0 or $\geq 1$

Where T and R7=C1-C22 alkyl

Where X⁻=halogen, hydroxide, alkoxide, sulfate or alkylsulfate

Examples of cationic monomers consist of aminoalkyl(meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyidialkyl ammonium salts; their mixtures, their salts, and macromonomers deriving from therefrom.

Further examples of cationic monomers include dimethylaminoethyl(meth)acrylate, dimethylaminopropyl(meth)acrylate, ditertiobutylaminoethyl(meth)acrylate, dimethylaminomethyl(meth)acrylamide, dimethylaminopropyl(meth)acrylamide; ethylenimine, vinylamine, 2-vinylpyridine, 4-vinylpyridine; trimethylammonium ethyl(meth)acrylate chloride, trimethylammonium ethyl(meth)acrylate methyl sulphate, dimethylammonium ethyl(meth)acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride, diallyldimethyl ammonium chloride.

Preferred cationic monomers comprise quaternary ammonium group of formula —NR$_3^+$, wherein R, which is identical or different, represents a hydrogen atom, an alkyl group comprising 1 to 10 carbon atoms, or a benzyl group, optionally carrying a hydroxyl group, and comprise an anion (counterion). Examples of anions are halides such as chloride and bromides, sulphates, hydrosulphates, alkylsulphates (for example comprising 1 to 6 carbon atoms), phosphates, citrates, formates, and acetates.

Preferred cationic monomers include trimethylammonium ethyl(meth)acrylate chloride, trimethylammonium ethyl(meth)acrylate methyl sulphate, dimethylammonium ethyl(meth)acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride.

More preferred cationic monomers include trimethyl ammonium propyl(meth)acrylamido chloride.

Where the monomer bearing a terminal negative charge is defined by R2'=H, C1-C4 linear or branched alkyl and R3 as:

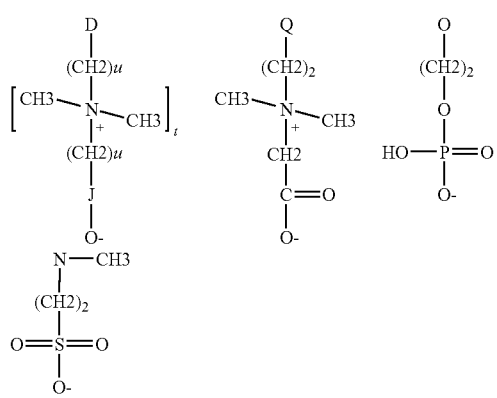

Where D=electronegative element chosen between oxygen, nitrogen, sulfur

Where Q=NH$_2$ or O

Where u=1-6

Where t=0-1

J=oxygenated functional group containing the following elements P, S, C

Examples of monomers bearing a terminal negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Preferred monomers with a terminal negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Where the functional nonionic monomer is defined by R2″=H, C1-C4 linear or branched alkyl, R6=linear or branched alkyl, alkyl aryl, aryl oxy, alkyloxy, alkylaryl oxy and β is defined as

Where G' and G″=O, S or N—H and L=0 or 1.

Examples of such nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide(meth)acrylate (i.e. polyethoxylated (meth)acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Preferred nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

The concentration of the cationic polymer in the shampoo composition ranges about 0.025% to about 5%, preferably from about 0.1% to about 3%, more preferably from about 0.2% to about 1%, by weight of the composition.

The anionic counterion (X⁻) in association with the cationic conditioning polymers may be any known counterion so long as the polymers remain soluble or dispersible in water, in the shampoo composition, or in a coacervate phase of the shampoo composition, and so long as the counterions are physically and chemically compatible with the essential components of the shampoo composition or do not otherwise unduly impair product performance, stability or aesthetics. Non limiting examples of such counterions include halides (e.g., chlorine, fluorine, bromine, iodine), sulfate and methylsulfate.

Homopolymer

The cationic polymer, by definition must contain cationic monomers and hence m must be greater than 1. However, in the case of homopolymers, there is only cationic monomers and hence p and q are zero. The homopolymer has either a cationic charge density of from about 2 meq/gm to about 4 meq/gm or a cationic charge density of at least 5 meq/gm or an average molecular weight of at least 500,000.

Highly preferred synthetic cationic homopolymers have high charge densities of from about 5 meq/gm to about 10 meq/gm. Other highly preferred synthetic cationic homopolymers have high charge densities of from about 7 meq/gm to about 10 meq/gm. The following structures are highly preferred synthetic cationic homopolymers. In the case of R1=CH3, the charge density is 5.60 when n=1. (Methacryloamidopropyl-pentamethyl-1,3-propylene-2-ol-ammonium dichloride example 6), in the case or R1=CH3, the charge density is 6.07 when n=2 (N,N,N,N',N',N'',N''-heptamethyl-N''-3-(1-oxo-2-methyl-2-propenyl)aminopropyl-9-oxo-8-azo-decane-1,4,10-triammonium trichloride. example 7) and in the case of R1=H, the charge density is 4.88 when n=0 (example 8).

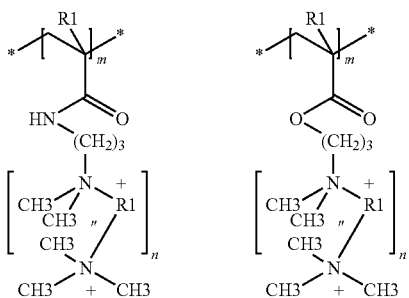

Another class of highly preferred homopolymers have an average molecular weight of about 500,000 to about 5 million, preferably from about 500,000 to about 2,000,000, and more preferably from about 750,000 to about 1,250,000. A highly preferred homopolymer conforms to the following structure (Examples 1-5):

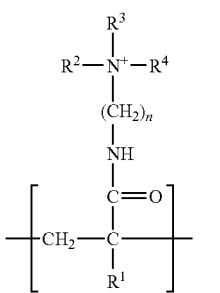

wherein $R^1$ is hydrogen, methyl or ethyl; each of $R^2$, $R^3$ and $R^4$ are independently hydrogen or a short chain alkyl having from about 1 to about 8 carbon atoms, preferably from about 1 to about 5 carbon atoms, more preferably from about 1 to about 2 carbon atoms; n is an integer having a value of from about 1 to about 8, preferably from about 1 to about 4; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups.

Copolymers

The copolymer formed from one or more cationic monomer units and one or more momomer units bearing a terminal negative charge or a functional nonionic momomer, wherein the subsequent charge of the copolymer is positive. In the case of the preferred copolymers p and/or q are greater than 1. In the case that there are monomers with units bearing a terminal negative charge, the overall polymer should be positive in charge and hence m>p.

A highly preferred synthetic cationic copolymer has charge densities of from about 2 meq/gm to about 10 meq/gm, preferably from about 3 meq/gm to about 8 meq/gm.

Another class of highly preferred copolymers has an average molecular weight of about 1,000 to about 5,000,000, preferably from about 100,000 to about 2,000,000

Examples of highly preferred copolymers include (these being exemplified in examples 11-15):

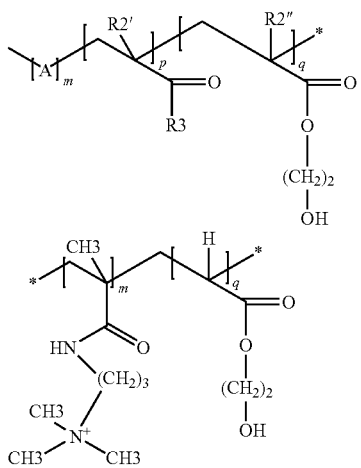

and (these being further exemplified in examples 16, 17 and 19):

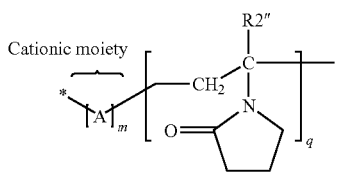

Where A, may be one or more of the following cationic moieties:

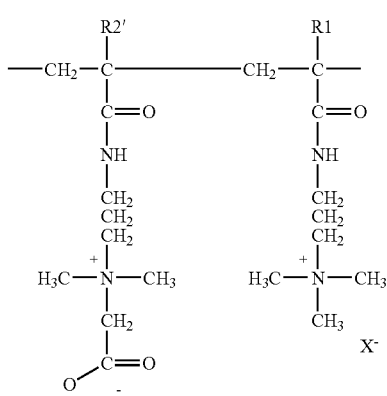

-continued

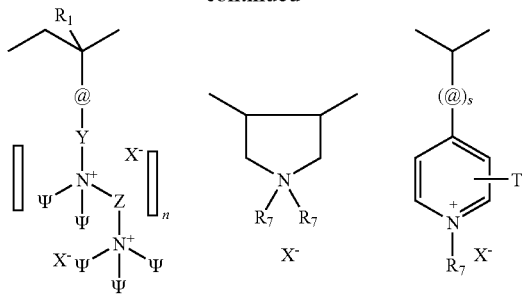

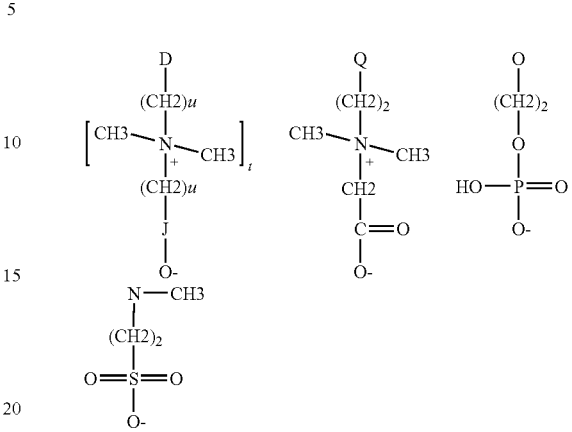

Where @=amido, alkylamido, ester, ether, alkyl or alkylaryl.

Where Y=C1-C22 alkyl, alkoxy, alkylidene, alkyl or aryloxy

Where ψ=C1-C22 alkyl, alkyloxy, alkyl aryl or alkyl aryloxy

Where Z=C1-C22 alkyl, alkyloxy, aryl or aryloxy

Where R1=H, C1-C4 linear or branched alkyl

Where s=0 or 1, n=0 or ≧1

Where T and R7=C1-C22 alkyl

Where X⁻=halogeno, hydroxide, alkoxide, sulfate or alkylsulfate

Examples of cationic monomers consist of aminoalkyl(meth)acrylates, (meth)aminoalkyl (meth)acrylamides; monomers comprising at least one secondary, tertiary or quaternary amine function, or a heterocyclic group containing a nitrogen atom, vinylamine or ethylenimine; diallyidialkyl ammonium salts; their mixtures, their salts, and macromonomers deriving from therefrom.

Further examples of cationic monomers include dimethylaminoethyl(meth)acrylate, dimethylaminopropyl(meth)acrylate, ditertiobutylaminoethyl(meth)acrylate, dimethylaminomethyl(meth)acrylamide, dimethylaminopropyl(meth)acrylamide; ethylenimine, vinylamine, 2-vinylpyridine, 4-vinylpyridine; trimethylammonium ethyl (meth)acrylate chloride, trimethylammonium ethyl(meth)acrylate methyl sulphate, dimethylammonium ethyl(meth)acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride, diallyidimethyl ammonium chloride.

Preferred cationic monomers comprise quaternary ammonium group of formula —NR₃⁺, wherein R, which is identical or different, represents a hydrogen atom, an alkyl group comprising 1 to 10 carbon atoms, or a benzyl group, optionally carrying a hydroxyl group, and comprise an anion (counterion). Examples of anions are halides such as chloride and bromides, sulphates, hydrosulphates, alkylsulphates (for example comprising 1 to 6 carbon atoms), phosphates, citrates, formates, and acetates.

Preferred cationic monomers include trimethylammonium ethyl(meth)acrylate chloride, trimethylammonium ethyl (meth)acrylate methyl sulphate, dimethylammonium ethyl (meth)acrylate benzyl chloride, 4-benzoylbenzyl dimethylammonium ethyl acrylate chloride, trimethyl ammonium ethyl(meth)acrylamido chloride, trimethyl ammonium propyl(meth)acrylamido chloride, vinylbenzyl trimethyl ammonium chloride.

More preferred cationic monomers include trimethyl ammonium propyl(meth)acrylamido chloride.

Where the monomer bearing a terminal negative charge is defined by R2'=H, C1-C4 linear or branched alkyl and R3 as:

Where D=electronegative element chosen between oxygen, nitrogen, sulfur

Where Q=NH2 or O

Where u=1-6

Where t=0-1

J=oxygenated functional group containing the following elements P, S, C

Examples of monomers bearing a terminal negative charge include alpha ethylenically unsaturated monomers comprising a phosphate or phosphonate group, alpha ethylenically unsaturated monocarboxylic acids, monoalkylesters of alpha ethylenically unsaturated dicarboxylic acids, monoalkylamides of alpha ethylenically unsaturated dicarboxylic acids, alpha ethylenically unsaturated compounds comprising a sulphonic acid group, and salts of alpha ethylenically unsaturated compounds comprising a sulphonic acid group.

Preferred monomers with a terminal negative charge include acrylic acid, methacrylic acid, vinyl sulphonic acid, salts of vinyl sulfonic acid, vinylbenzene sulphonic acid, salts of vinylbenzene sulphonic acid, alpha-acrylamidomethylpropanesulphonic acid, salts of alpha-acrylamidomethylpropanesulphonic acid, 2-sulphoethyl methacrylate, salts of 2-sulphoethyl methacrylate, acrylamido-2-methylpropanesulphonic acid (AMPS), salts of acrylamido-2-methylpropanesulphonic acid, and styrenesulphonate (SS).

Where the functional nonionic monomer is defined by R2"=H, C1-C4 linear or branched alkyl, R6=linear or branched alkyl, alkyl aryl, aryl oxy, alkyloxy, alkylaryl oxy and V is defined as

Where G' and G"=O, S or N—H and L=0 or 1.

Examples of such nonionic monomers include vinyl acetate, amides of alpha ethylenically unsaturated carboxylic acids, esters of an alpha ethylenically unsaturated monocarboxylic acids with an hydrogenated or fluorinated alcohol, polyethylene oxide(meth)acrylate (i.e. polyethoxylated (meth)acrylic acid), monoalkylesters of alpha ethylenically unsaturated dicarboxylic acids, monoalkylamides of alpha ethylenically unsaturated dicarboxylic acids, vinyl nitriles, vinylamine amides, vinyl alcohol, vinyl pyrolidone, and vinyl aromatic compounds.

Preferred nonionic monomers include styrene, acrylamide, methacrylamide, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethyl-hexyl methacrylate, 2-hydroxyethylacrylate and 2-hydroxyethylmethacrylate.

Aqueous Carrier

The compositions of the present invention are typically in the form of pourable liquids (under ambient conditions). The compositions will therefore typically comprise an aqueous carrier, which is present at a level of from about 20% to about 95%, preferably from about 60% to about 85%, by weight of the compositions. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

Optional Components

Conditioning Agent

Conditioning agents include any material which is used to give a particular conditioning benefit to hair and/or skin. In hair treatment compositions, suitable conditioning agents are those which deliver one or more benefits relating to shine, softness, combability, antistatic properties, wet-handling, damage, manageability, body, and greasiness. The conditioning agents useful in the personal cleansing compositions of the present invention typically comprise a water insoluble, water dispersible, non-volatile, liquid that forms emulsified, liquid particles or are solubilized by the surfactant micelles, in the anionic detersive surfactant component (described above). Suitable conditioning agents for use in the personal cleansing composition are those conditioning agents characterized generally as silicones (e.g. silicone oils, cationic silicones, silicone gums, high refractive silicones, and silicone resins), organic conditioning oils (e.g. hydrocarbon oils, polyolefins, and fatty esters) or combinations thereof, or those conditioning agents which otherwise form liquid, dispersed, particles in the aqueous surfactant matrix herein. Such conditioning agents should be physically and chemically compatible with the essential components of the composition, and should not otherwise unduly impair product stability, aesthetics or performance.

The concentration of the conditioning agent in the personal cleansing composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

1. Silicones

The conditioning agent of the personal cleansing compositions of the present invention is preferably an insoluble silicone conditioning agent. The silicone conditioning agent particles may comprise volatile silicone, non-volatile silicone, or combinations thereof. Preferred are non-volatile silicone conditioning agents. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair (especially when high refractive index (e.g. above about 1.46) silicone conditioning agents are used (e.g. highly phenylated silicones).

The concentration of the silicone conditioning agent typically ranges from about 0.01% to about 10%, by weight of the composition, preferably from about 0.1% to about 8%, more preferably from about 0.1% to about 5%, more preferably from about 0.2% to about 3%. Non-limiting examples of suitable silicone conditioning agents, and optional suspending agents for the silicone, are described in U.S. Reissue Pat. Nos. 34,584, 5,104,646, and 5,106,609, which descriptions are incorporated herein by reference. The silicone conditioning agents for use in the personal cleansing compositions of the present invention preferably have a viscosity, as measured at 25° C., from about 20 to about 2,000,000 centistokes ("csk"), more preferably from about 1,000 to about 1,800,000 csk, even more preferably from about 50,000 to about 1,500,000 csk, more preferably from about 100,000 to about 1,500,000 csk.

The dispersed silicone conditioning agent particles typically have a volume average particle diameter ranging from about 5 µm to about 125 µm. For small particle application to hair, the volume average particle diameters typically range from about 0.01 µm to about 4 µm, preferably from about 0.01 µm to about 2 µm, more preferably from about 0.01 µm to about 0.5 µm. For larger particle application to hair, the volume average particle diameters typically range from about 5 µm to about 125 µm, preferably from about 10 µm to about 90 µm, more preferably from about 15 µm to about 70 µm, more preferably from about 20 µm to about 50 µm.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

a. Silicone Oils

Silicone fluids include silicone oils, which are flowable silicone materials having a viscosity, as measured at 25° C., less than 1,000,000 csk, preferably from about 5 csk to about 1,000,000 csk, more preferably from about 10 csk to about 100,000 csk. Suitable silicone oils for use in the personal cleansing compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

Silicone oils include polyalkyl or polyaryl siloxanes which conform to the following Formula (I):

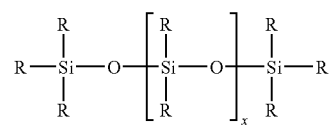

wherein R is aliphatic, preferably alkyl or alkenyl, or aryl, R can be substituted or unsubstituted, and x is an integer from 1 to about 8,000. Suitable unsubstituted R groups for use in the personal cleansing compositions of the present invention include, but are not limited to: alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

Preferred alkyl and alkenyl substituents are $C_1$ to $C_5$ alkyls and alkenyls, more preferably from $C_1$ to $C_4$, more preferably from $C_1$ to $C_2$. The aliphatic portions of other alkyl-, alkenyl-, or alkynyl-containing groups (such as alkoxy, alkaryl, and alkamino) can be straight or branched chains, and are preferably from $C_1$ to $C_5$, more preferably from $C_1$ to $C_4$, even more preferably from $C_1$ to $C_3$, more preferably from $C_1$ to $C_2$. As discussed above, the R substituents can also contain amino functionalities (e.g. alkamino groups), which can be primary, secondary or tertiary amines or quaternary ammonium. These include mono-, di- and tri-alkylamino and alkoxyamino groups, wherein the aliphatic portion chain length is preferably as described above.

b. Cationic Silicones

Cationic silicone fluids suitable for use in the personal cleansing compositions of the present invention include, but are not limited to, those which conform to the general formula (II):

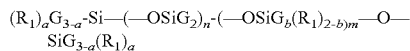

wherein G is hydrogen, phenyl, hydroxy, or $C_1$-$C_8$ alkyl, preferably methyl; a is 0 or an integer having a value from 1 to 3, preferably 0; b is 0 or 1, preferably 1; n is a number from 0 to 1,999, preferably from 49 to 149; m is an integer from 1 to 2,000, preferably from 1 to 10; the sum of n and m is a number from 1 to 2,000, preferably from 50 to 500; $R_1$ is a monovalent radical conforming to the general formula $CqH_{2q}L$, wherein q is an integer having a value from 2 to 8 and L is selected from the following groups:

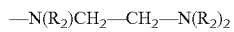

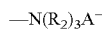

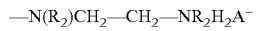

wherein $R_2$ is hydrogen, phenyl, benzyl, or a saturated hydrocarbon radical, preferably an alkyl radical from about $C_1$ to about $C_{20}$, and $A^-$ is a halide ion.

An especially preferred cationic silicone corresponding to formula (II) is the polymer known as "trimethylsilylamodimethicone", which is shown below in formula (III):

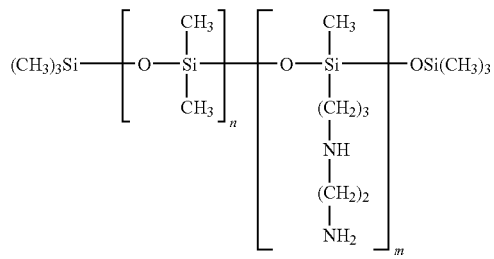

Other Silicone Cationic Polymers which May be Used in the Personal Cleansing Compositions of the present invention are represented by the general formula (IV):

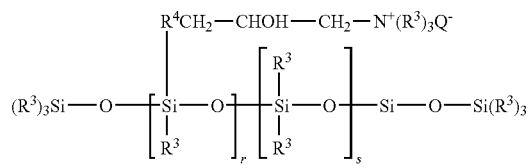

wherein $R^3$ is a monovalent hydrocarbon radical from $C_1$ to $C_{18}$, preferably an alkyl or alkenyl radical, such as methyl; $R_4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; $Q^-$ is a halide ion, preferably chloride; r is an average statistical value from 2 to 20, preferably from 2 to 8; s is an average statistical value from 20 to 200, preferably from 20 to 50. A preferred polymer of this class is known as UCARE SILICONE ALE 56™, available from Union Carbide.

c. Silicone Gums

Other silicone fluids suitable for use in the personal cleansing compositions of the present invention are the insoluble silicone gums. These gums are polyorganosiloxane materials having a viscosity, as measured at 25° C., of greater than or equal to 1,000,000 csk. Silicone gums are described in U.S. Pat. No. 4,152,416; Noll and Walter, *Chemistry and Technology of Silicones*, New York: Academic Press (1968); and in General Electric Silicone Rubber Product Data Sheets SE 30, SE 33, SE 54 and SE 76, all of which are incorporated herein by reference. The silicone gums will typically have a weight average molecular weight in excess of about 200,000, preferably from about 200,000 to about 1,000,000. Specific non-limiting examples of silicone gums for use in the personal cleansing compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

d. High Refractive Index Silicones

Other non-volatile, insoluble silicone fluid conditioning agents that are suitable for use in the personal cleansing compositions of the present invention are those known as "high refractive index silicones," having a refractive index of at least about 1.46, preferably at least about 1.48, more preferably at least about 1.52, more preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (I) above, as well as cyclic polysiloxanes such as those represented by Formula (V) below:

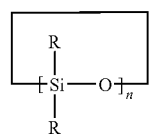

wherein R is as defined above, and n is a number from about 3 to about 7, preferably from about 3 to about 5.

The high refractive index polysiloxane fluids contain an amount of aryl-containing R substituents sufficient to increase the refractive index to the desired level, which is described above. Additionally, R and n must be selected so that the material is non-volatile.

Aryl-containing substituents include those which contain alicyclic and heterocyclic five and six member aryl rings and those which contain fused five or six member rings. The aryl rings themselves can be substituted or unsubstituted.

Generally, the high refractive index polysiloxane fluids will have a degree of aryl-containing substituents of at least about 15%, preferably at least about 20%, more preferably at least about 25%, even more preferably at least about 35%, more preferably at least about 50%. Typically, the degree of aryl substitution will be less than about 90%, more generally less than about 85%, preferably from about 55% to about 80%.

Preferred high refractive index polysiloxane fluids have a combination of phenyl or phenyl derivative substituents (more preferably phenyl), with alkyl substituents, preferably $C_1$-$C_4$ alkyl (more preferably methyl), hydroxy, or $C_1$-$C_4$ alkylamino (especially —$R^1NHR^2NH2$ wherein each $R^1$ and $R^2$ independently is a $C_1$-$C_3$ alkyl, alkenyl, and/or alkoxy).

When high refractive index silicones are used in the personal cleansing compositions of the present invention, they are preferably used in solution with a spreading agent, such as a silicone resin or a surfactant, to reduce the surface tension by a sufficient amount to enhance spreading and thereby enhance the glossiness (subsequent to drying) of hair treated with the compositions.

Silicone fluids suitable for use in the personal cleansing compositions of the present invention are disclosed in U.S. Pat. Nos. 2,826,551, 3,964,500, 4,364,837, British Pat. No. 849,433, and *Silicon Compounds*, Petrarch Systems, Inc. (1984), all of which are incorporated herein by reference.

e. Silicone Resins

Silicone resins may be included in the silicone conditioning agent of the personal cleansing compositions of the present invention. These resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetra-functional unit $SiO_2$. Primes of the unit symbols (e.g. M', D', T', and Q') denote substituents other than methyl, and must be specifically defined for each occurrence.

Preferred silicone resins for use in the personal cleansing compositions of the present invention include, but are not limited to MQ, MT, MTQ, MDT and MDTQ resins. Methyl is a preferred silicone substituent. Especially preferred silicone resins are MQ resins, wherein the M:Q ratio is from about 0.5:1.0 to about 1.5:1.0 and the average molecular weight of the silicone resin is from about 1000 to about 10,000.

The weight ratio of the non-volatile silicone fluid, having refractive index below 1.46, to the silicone resin component, when used, is preferably from about 4:1 to about 400:1, more preferably from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

2. Organic Conditioning Oils

The conditioning component of the personal cleansing compositions of the present invention may also comprise from about 0.05% to about 3%, by weight of the composition, preferably from about 0.08% to about 1.5%, more preferably from about 0.1% to about 1%, of at least one organic conditioning oil as the conditioning agent, either alone or in combination with other conditioning agents, such as the silicones (described above).

a. Hydrocarbon Oils

Suitable organic conditioning oils for use as conditioning agents in the personal cleansing compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

Specific non-limiting examples of these hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, polybutene, polydecene, and mixtures thereof. Branched-chain isomers of these compounds, as well as of higher chain length hydrocarbons, can also be used, examples of which include highly branched, saturated or unsaturated, alkanes such as the permethyl-substituted isomers, e.g., the permethyl-substituted isomers of hexadecane and eicosane, such as 2, 2, 4, 4, 6, 6, 8, 8-dimethyl-10-methylundecane and 2, 2, 4, 4, 6, 6-dimethyl-8-methylnonane, available from Permethyl Corporation. Hydrocarbon polymers such as polybutene and polydecene. A preferred hydrocarbon polymer is polybutene, such as the copolymer of isobutylene and butene. A commercially available material of this type is L-14 polybutene from Amoco Chemical Corporation.

b. Polyolefins

Organic conditioning oils for use in the personal cleansing compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

Non-limiting examples of olefenic monomers for use in preparing the polyolefin liquids herein include ethylene, propylene, 1-butene, 1-pentene, 1-hexene, 1-octene, 1-decene, 1-dodecene, 1-tetradecene, branched chain isomers such as 4-methyl-1-pentene, and mixtures thereof. Also suitable for preparing the polyolefin liquids are olefin-containing refinery feedstocks or effluents. Preferred hydrogenated α-olefin monomers include, but are not limited to: 1-hexene to 1-hexadecenes, 1-octene to 1-tetradecene, and mixtures thereof.

c. Fatty Esters

Other suitable organic conditioning oils for use as the conditioning agent in the personal cleansing compositions of the present invention include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Specific examples of preferred fatty esters include, but are not limited to: isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Other fatty esters suitable for use in the personal cleansing compositions of the present invention are mono-carboxylic acid esters of the general formula R'COOR, wherein R' and R are alkyl or alkenyl radicals, and the sum of carbon atoms in R' and R is at least 10, preferably at least 22.

Still other fatty esters suitable for use in the personal cleansing compositions of the present invention are di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, adipic acid). Specific non-limiting examples of di- and tri-alkyl and alkenyl esters of carboxylic acids include isocetyl stearyol stearate, diisopropyl adipate, and tristearyl citrate.

Other fatty esters suitable for use in the personal cleansing compositions of the present invention are those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other fatty esters suitable for use in the personal cleansing compositions of the present invention are glycerides, including, but not limited to, mono-, di-, and tri-glycerides, preferably di- and tri-glycerides, more preferably triglycerides. For use in the personal cleansing compositions described herein, the glycerides are preferably the mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, lanolin and soybean oil. Synthetic oils include, but are not limited to, triolein and tristearin glyceryl dilaurate.

Other fatty esters suitable for use in the personal cleansing compositions of the present invention are water insoluble synthetic fatty esters. Some preferred synthetic esters conform to the general Formula (VI):

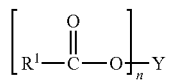

wherein $R^1$ is a $C_7$ to $C_9$ alkyl, alkenyl, hydroxyalkyl or hydroxyalkenyl group, preferably a saturated alkyl group, more preferably a saturated, linear, alkyl group; n is a positive integer having a value from 2 to 4, preferably 3; and Y is an alkyl, alkenyl, hydroxy or carboxy substituted alkyl or alkenyl, having from about 2 to about 20 carbon atoms, preferably from about 3 to about 14 carbon atoms. Other preferred synthetic esters conform to the general Formula (VII):

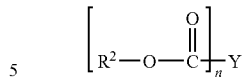

wherein $R^2$ is a $C_8$ to $C_{10}$ alkyl, alkenyl, hydroxyalkyl or hydroxyalkenyl group; preferably a saturated alkyl group, more preferably a saturated, linear, alkyl group; n and Y are as defined above in Formula (VII).

Specific non-limiting examples of suitable synthetic fatty esters for use in the personal cleansing compositions of the present invention include: P-43 ($C_8$-$C_{10}$ triester of trimethylolpropane), MCP-684 (tetraester of 3,3 diethanol-1,5 pentadiol), MCP 121 ($C_8$-$C_{10}$ diester of adipic acid), all of which are available from Mobil Chemical Company.

3. Other Conditioning Agents

Also suitable for use in the compositions herein are the conditioning agents described by the Procter & Gamble Company in U.S. Pat. Nos. 5,674,478, and 5,750,122, both of which are incorporated herein in their entirety by reference. Also suitable for use herein are those conditioning agents described in U.S. Pat. No. 4,529,586 (Clairol), U.S. Pat. No. 4,507,280 (Clairol), U.S. Pat. No. 4,663,158 (Clairol), U.S. Pat. No. 4,197,865 (L'Oreal), U.S. Pat. No. 4,217,914 (L'Oreal), U.S. Pat. No. 4,381,919 (L'Oreal), and U.S. Pat. No. 4,422,853 (L'Oreal), all of which descriptions are incorporated herein by reference.

Phase Separation Initiator

The personal cleansing compositions of the present invention may further comprise a phase separation initiator. By the term "phase separation initiators", as used herein, means electrolytes, amphiphiles or mixtures thereof capable of inducing phase separation when combined with compositions comprising an anionic detersive surfactant component surfactant system and the synthetic cationic polymer.

By the term "amphiphile" as used herein, means, generally, substances which contain both hydrophilic and hydrophobic (lipophilic) groups. Amphiphiles preferred for use in the present invention are those which generally do not form micelles or liquid crystal phases and include, but are not limited to: amides of fatty acids; fatty alcohols; fatty esters, glycyl mono- and di-esters of fatty acids; glyceryl esters.

Yet another class of particularly useful amphiphiles are fragrances. Typically "fragrance raw materials" comprise inter alia alcohols, ketones, aldehydes, esters, ethers, nitrites, and cyclic and acyclic alkenes such as terpenes. A listing of common "fragrance raw materials" can be found in various reference sources, for example, "Perfume and Flavor Chemicals", Vols. I and II; Steffen Arctander Allured Pub. Co. (1994), "Perfumes: Art, Science and Technology"; Muller, P. M. and Lamparsky, D., Blackie Academic and Professional (1994) and U.S. Pat. No. 6,087,322 to Morelli et al., incorporated herein by reference. The phase separation initiator is incorporated in liquid crystals, and is therefore deposited on the hair, giving greater fragrance longevity to the skin or hair.

Amides, including alkanol amides, are the condensation products of fatty acids with primary and secondary amines or alkanolamines to yield products of the general formula:

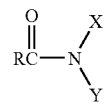

wherein RCO is a fatty acid radical and R is $C_{8-20}$; X is an alkyl, aromatic or alkanol (CHR'CH$_2$OH wherein R' is H or $C_{1-6}$ alkyl); Y is H, alkyl, alkanol or X. Suitable amides include, but are not limited to, cocamide, lauramide, oleamide and stearamide. Suitable alkanolamides include, but are not limited to, cocamide DEA, cocamide MEA, cocamide MIPA, isostearamide DEA, isostearamide MEA, isostearamide MIPA, lanolinamide DEA, lauramide DEA, lauramide MEA, lauramide MIPA, linoleamide DEA, linoleamide MEA, linoleamide MIPA, myristamide DEA, myristamide MEA, myristamide MIPA, Oleamide DEA, Oleamide MEA, Oleamide MIPA, palmamide DEA, palmamide MEA, palmamide MIPA, palmitamide DEA, palmitamide MEA, palm kernelamide DEA, palm kernelamide MEA, palm kernelamide MIPA, peanutamide MEA, peanutamide MIPA, soyamide DEA, stearamide DEA, stearamide MEA, stearamide MIPA, tallamide DEA, tallowamide DEA, tallowamide MEA, undecylenamide DEA, undecylenamide MEA. The condensation reaction may be carried out with free fatty acids or with all types of esters of the fatty acids, such as fats and oils, and particularly methyl esters. The reaction conditions and the raw material sources determine the blend of materials in the end product and the nature of any impurities.

Fatty alcohols are higher molecular weight, nonvolatile, primary alcohols having the general formula:

$$RCH_2OH$$

wherein R is a $C_{8-20}$ alkyl. They can be produced from natural fats and oils by reduction of the fatty acid COOH— grouping to the hydroxyl function. Alternatively, identical or similarly structured fatty alcohols can be produced according to conventional synthetic methods known in the art. Suitable fatty alcohols include, but are not limited to, behenyl alcohol, $C_{9-11}$ alcohols, $C_{12-13}$ alcohols, $C_{12-15}$ alcohols, $C_{12-16}$ alcohols, $C_{14-15}$ alcohols, caprylic alcohol, cetearyl alcohol, coconut alcohol, decyl alcohol, isocetyl alcohol, isostearyl alcohol, lauryl alcohol, oleyl alcohol, palm kernel alcohol, stearyl alcohol, cetyl alcohol, tallow alcohol, tridecyl alcohol or myristyl alcohol.

Glyceryl esters comprise a subgroup of esters which are primarily fatty acid mono- and di-glycerides or triglycerides modified by reaction with other alcohols and the like. Preferred glyceryl esters are mono and diglycerides. Suitable glyceryl esters and derivatives thereof include, but are not limited to, acetylated hydrogenated tallow glyceride, glyceryl behenate, glyceryl caprate, glyceryl caprylate, glyceryl caprylate/caprate, glyceryl dilaurate, glyceryl dioleate, glyceryl erucate, glyceryl hydroxystearate, glyceryl isostearate, glyceryl lanolate, glyceryl laurate, glyceryl linoleate, glyceryl oleate, glyceryl stearate, glyceryl myristate, glyceryl distearate and mixtures thereof, Also useful as amphiphiles in the present invention are long chain glycol esters or mixtures thereof. Included are ethylene glycol esters of fatty acids having from about 8 to about 22 carbon atoms. Fatty esters of the formula RCO—OR' also act as suitable amphiphiles in the compositions of the present invention, where one of R and R' is a $C_{8-22}$ alkyl and the other is a $C_{1-3}$ alkyl.

The amphiphiles of the present invention may also encompass a variety of surface active compounds such as nonionic and cationic surfactants. If incorporated into the compositions of the present invention, these surface active compounds become additional surfactants used as amphilphiles for the purpose of initiating phase separation and are separate and apart from the surfactants of the surfactant system and the alkyl glyceryl sulfonate surfactant of the present invention.

Amphiphiles preferred for use herein include cocamide MEA, cetyl alcohol and stearyl alcohol.

The amphiphiles of the present invention are preferably present in the personal cleansing compositions at levels of from 0 to about 4%, preferably from about 0.5% to about 2%.

Suitable electrolytes include mono-, di- and trivalent inorganic salts as well as organic salts. Surfactant salts themselves are not included in the present electrolyte definition but other salts are. Suitable salts include, but are not limited to, phosphates, sulfates, nitrates, citrates and halides. The counter ions of such salts can be, but are not limited to, sodium, potassium, ammonium, magnesium or other mono-, di and tri valent cation. Electrolytes most preferred for use in the compositions of the present invention include sodium chloride, ammonium chloride, sodium citrate, and magnesium sulfate. It is recognized that these salts may serve as thickening aids or buffering aids in addition to their role as a phase separation initiator. The amount of the electrolyte used will generally depend on the amount of the amphiphile incorporated, but may be used at concentration levels of from about 0.1% to about 4%, preferably from about 0.2% to about 2%. More preferably, less than 2% of electrolyte is used in the cleansing composition of the present invention. Even more preferably, less than 1% of electrolyte is used in the cleansing composition of the present invention.

The amount of phase separation initiator comprising the electrolyte and/or the amphiphile will vary with the type of surfactant and polymer, but is preferably present at a level of from about 0.1% to about 5%, more preferably from about 0.1% to about 4%, still more preferably from about 0.5% to about 4%, and yet more preferably from about 1% to about 3%.

In view of the highly preferred nature and activity of the phase separation initiators described above, the compositions of the present invention are, preferably, substantially free of materials which would prevent the induction or formation of separate, liquid phases. The term "substantially free", as used here, means that the compositions of the present invention contain no more than about 0.5% of such materials, preferably less than 0.25%, more preferably zero. Such materials typically include ethylene glycol, propylene glycol, ethyl alcohol and the like.

The compositions of the present invention are also preferably substantially free of other ingredients which unduly minimize the formation of separate and distinct liquid phases, especially ingredients which do not provide a significant benefit to the present invention.

Suspending Agent

The shampoo compositions of the present invention may further comprise a suspending agent at concentrations effective for suspending the polymeric liquid crystal or the dispersed particles of a water insoluble, conditioning agent, or other water-insoluble, dispersed material in the shampoo compositions. Such concentrations range from about 0.1% to about 10%, preferably from about 0.3% to about 5.0%, by weight of the shampoo compositions.

Suitable suspending agents include crystalline suspending agents that can be categorized as acyl derivatives, long chain amine oxides, or combinations thereof. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$-$C_{22}$ chains may be used.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl ($C_{16}$-$C_{22}$) dimethyl amine oxides, e.g., stearyl dimethyl amine oxide Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow) amine. Still other suitable suspending agents include di(hydrogenated tallow)phthalic acid amide, and crosslinked maleic anhydride-methyl vinyl ether copolymer.

Additional Components

Dispersed Particles

The composition of the present invention may include dispersed particles. In the compositions of the present invention, it is preferable to incorporate at least 0.025% by weight of the dispersed particles, more preferably at least 0.05%, still more preferably at least 0.1%, even more preferably at least 0.25%, and yet more preferably at least 0.5% by weight of the dispersed particles. In the compositions of the present invention, it is preferable to incorporate no more than about 20% by weight of the dispersed particles, more preferably no more than about 10%, still more preferably no more than 5%, even more preferably no more than 3%, and yet more preferably no more than 2% by weight of the dispersed particles.

Anti-dandruff Actives

The compositions of the present invention may also contain an anti-dandruff agent. Suitable, non-limiting examples of anti-dandruff particulates include: pyridinethione salts, azoles, selenium sulfide, particulate sulfur, and mixtures thereof. Preferred are pyridinethione salts. Such anti-dandruff particulate should be physically and chemically compatible with the essential components of the composition, and should not otherwise unduly impair product stability, aesthetics or performance.

Pyridinethione Salts

Pyridinethione anti-dandruff particulates, especially 1-hydroxy-2-pyridinethione salts, are highly preferred particulate anti-dandruff agents for use in compositions of the present invention. The concentration of pyridinethione anti-dandruff particulate typically ranges from about 0.1% to about 4%, by weight of the composition, preferably from about 0.1% to about 3%, more preferably from about 0.3% to about 2%. Preferred pyridinethione salts include those formed from heavy metals such as zinc, tin, cadmium, magnesium, aluminum and zirconium, preferably zinc, more preferably the zinc salt of 1-hydroxy-2-pyridinethione (known as "zinc pyridinethione" or "ZPT"), more preferably 1-hydroxy-2-pyridinethione salts in platelet particle form, wherein the particles have an average size of up to about 20µ, preferably up to about 5µ, more preferably up to about 2.5µ. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982, all of which are incorporated herein by reference. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

Other Anti-microbial Actives—In addition to the anti-dandruff active selected from polyvalent metal salts of pyrithione, the present invention may further comprise one or more anti-fungal or anti-microbial actives in addition to the metal pyrithione salt actives. Suitable anti-microbial actives include coal tar, sulfur, whitfield's ointment, castellani's paint, aluminum chloride, gentian violet, octopirox (piroctone olamine), ciclopirox olamine, undecylenic acid and it's metal salts, potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Preferred anti-microbials include itraconazole, ketoconazole, selenium sulphide and coal tar.

Azoles

Azole anti-microbials include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof. When present in the composition, the azole anti-microbial active is included in an amount from about 0.01% to about 5%, preferably from about 0.1% to about 3%, and more preferably from about 0.3% to about 2%, by weight of the composition. Especially preferred herein is ketoconazole.

Selenium Sulfide

Selenium sulfide is a particulate anti-dandruff agent suitable for use in the anti-microbial compositions of the present invention, effective concentrations of which range from about 0.1% to about 4%, by weight of the composition, preferably from about 0.3% to about 2.5%, more preferably from about 0.5% to about 1.5%. Selenium sulfide is generally regarded as a compound having one mole of selenium and two moles of sulfur, although it may also be a cyclic structure that conforms to the general formula $Se_xS_y$, wherein x+y=8. Average particle diameters for the selenium sulfide are typically less than 15 µm, as measured by forward laser light scattering device (e.g. Malvern 3600 instrument), preferably less than 10 µm. Selenium sulfide compounds are described, for example, in U.S. Pat. Nos. 2,694,668; 3,152,046; 4,089,945; and 4,885,107, all of which descriptions are incorporated herein by reference.

Sulfur

Sulfur may also be used as a particulate anti-microbial/anti-dandruff agent in the anti-microbial compositions of the present invention. Effective concentrations of the particulate sulfur are typically from about 1% to about 4%, by weight of the composition, preferably from about 2% to about 4%.

Keratolytic Agents

The present invention may further comprise one or more keratolytic agents such as Salicylic Acid.

Additional anti-microbial actives of the present invention may include extracts of melaleuca (tea tree) and charcoal. The present invention may also comprise combinations of anti-microbial actives. Such combinations may include octopirox and zinc pyrithione combinations, pine tar and sulfur combinations, salicylic acid and zinc pyrithione combinations, octopirox and climbasole combinations, and salicylic acid and octopirox combinations, and mixtures thereof.

Humectant

The compositions of the present invention may contain a humectant. The humectants herein are selected from the group consisting of polyhydric alcohols, water soluble alkoxylated nonionic polymers, and mixtures thereof. The humectants, when used herein, are preferably used at levels by weight of the composition of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

Other Optional Components

The compositions of the present invention may contain also vitamins and amino acids such as: water soluble vitamins such as vitamin B1, B2, B6, B12, C, pantothenic acid, pantothenyl ethyl ether, panthenol, biotin, and their derivatives, water soluble amino acids such as asparagine, alanin, indole, glutamic acid and their salts, water insoluble vitamins such as vitamin A, D, E, and their derivatives, water insoluble amino acids such as tyrosine, tryptamine, and their salts.

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocianine, botanical, natural colors, including: water soluble components such as those having C. I. Names. The compositions of the present invention may also contain antimicrobial agents which are useful as cosmetic biocides and antidandruff agents including: water soluble components such as piroctone olamine, water insoluble components such as 3,4,4'-trichlorocarbanilide (trichlosan), triclocarban and zinc pyrithione. The compositions of the present invention may also contain chelating agents.

Method of Manufacture

The compositions of the present invention, in general, may be made by mixing together at elevated temperature, e.g., about 72.degree. C. water and surfactants along with any solids (e.g. amphiphiles) that need to be melted, to speed mixing into the personal cleansing composition. The ingredients are mixed thoroughly at the elevated temperature and then cooled to ambient temperature. Additional ingredients, including electrolytes, polymers, and particles, may be added to the cooled product. The silicone may be emulsified at room temperature in concentrated surfactant and then added to the cooled product.

Method of Use

The shampoo compositions of the present invention are used in a conventional manner for cleansing and conditioning hair or skin. An effective amount of the composition for cleansing and conditioning the hair or skin is applied to the hair or skin, that has preferably been wetted with water, and then rinsed off. Such effective amounts generally range from about 1 gm to about 50 gm, preferably from about 1 gm to about 20 gm. Application to the hair typically includes working the composition through the hair such that most or all of the hair is contacted with the composition.

This method for cleansing and conditioning the hair or skin comprises the steps of: a) wetting the hair or skin with water, b) applying an effective amount of the shampoo composition to the hair or skin, and c) rinsing the applied areas of skin or hair with water. These steps can be repeated as many times as desired to achieve the desired cleansing and conditioning benefit.

Non-limiting Examples

| | Hompolymers | | | | |
| --- | --- | --- | --- | --- | --- |
| | EXAMPLE COMPOSITION | | | | |
| | 1 | 2 | 3 | 4 | 5 |
| Ammonium Laureth Sulfate (AE$_3$S) | 6.50 | 10.00 | | | 6.50 |
| Ammonium Lauryl Sulfate (ALS) | 8.10 | 6.00 | | | 5.50 |
| Sodium Laureth Sulfate (SE$_3$S) | | | 6.50 | 6.50 | |
| Sodium Lauryl Sulfate (SLS) | 1.40 | | 5.50 | 5.50 | |
| Sodium Lauroamphoacetate[14] | | | | | 2.00 |
| Cocaminopropionic Acid[15] | | | | 1.00 | |
| Cocamidopropyl Betaine[16] | | | | 1.00 | |
| Cocamide MEA | 1.00 | 0.80 | 0.80 | 0.80 | 0.80 |
| Cetyl Alcohol | 0.35 | 0.90 | 0.60 | 0.60 | 0.60 |
| Lauryl Alcohol | 0.20 | | 0.35 | 0.35 | 0.35 |
| Dihydrogenated Tallowamidoethyl Hydroxyethylmonium Methosulfate[17] | | | 0.15 | 0.15 | 0.15 |
| 1-Propanaminium, N,N,N-trimethyl-3-[(2-methyl-1-oxo-2-propenyl)amino]-, chloride; | 0.40[1] | 0.50[1] | 0.40[1] | 0.40[1] | 0.40[2] |

-continued

| Hompolymers | | | | | |
|---|---|---|---|---|---|
| (Poly(Methacrylamidopropyl trimethyl ammonium chloride))[1,2] | | | | | |
| Methacryloamidopropyl-pentamethyl-1,3-propylene-2-ol-ammonium dichloride[3] | | | | | |
| N,N,N,N',N',N'',N''-heptamethyl-N''-3-(1-oxo-2-methyl-2-propenyl)aminopropyl-9-oxo-8-azo-decane-1,4,10-triammonium trichloride (18) | | | | | |
| 1-Propanaminium, N,N,N-trimethyl-3-[(1-oxo-2-propenyl)amino]-, chloride; (Poly(Acrylamidopropyl trimethyl ammonium chloride))[4] | | | | | |
| [3-methacryloylamino)propyl] dimethylethylammonium ethylsulfate homopolymer[5] | | | | | |
| [(2-methacryloyloxy)ethyl]trimethylammonium methylsulfate homopolymer[6] | | | | | |
| Ethylene Glycol Distearate | | 1.50 | 1.50 | 1.50 | 1.50 |
| Trihydroxystearin[7] | 0.25 | | | | |
| Polyethylene Glycol (14000)[8] | | | 0.17 | 0.17 | 0.17 |
| Fragrance | 0.55 | 0.70 | 0.55 | 0.55 | 0.55 |
| Sodium Chloride | 0.30 | 1.30 | 0.80 | 0.80 | 0.80 |
| Ammonium Xylenesulfonate | 1.00 | | | | |
| Citric Acid | 0.04 | 0.04 | 0.04 | 0.04 | 0.04 |
| Sodium Citrate | 0.40 | 0.40 | 0.40 | 0.40 | 0.40 |
| Sodium Benzoate | 0.25 | 0.25 | 0.25 | 0.25 | 0.25 |
| Ethylene Diamine Tetra Acetic Acid | 0.10 | 0.10 | 0.10 | 0.10 | 0.10 |
| Dimethicone[9,10,11] | | 2.35[9] | 0.50[9] | 2.00[10] | 2.00[11] |
| Polydecene[12] | | 0.40 | | | |
| Trimethylolpropane Tricaprylate/Tricaprate[13] | | 0.10 | | | |
| Water and Minors (QS to 100%) | | | | | |

| | EXAMPLE COMPOSITION | | | | |
|---|---|---|---|---|---|
| | 6 | 7 | 8 | 9 | 10 |
| Ammonium Laureth Sulfate (AE₃S) | 7.5 | 7.5 | | | |
| Ammonium Lauryl Sulfate (ALS) | 6.5 | 6.5 | | | |
| Sodium Laureth Sulfate (SE₃S) | | | 6.50 | 6.50 | 6.50 |
| Sodium Lauryl Sulfate (SLS) | | | 5.50 | 5.50 | 5.50 |
| Sodium Lauroamphoacetate[14] | | | | 2.00 | |
| Cocaminopropionic Acid[15] | | | | | |
| Cocamidopropyl Betaine[16] | | | | | |
| Cocamide MEA | 0.80 | 0.80 | 0.80 | 0.80 | 0.80 |
| Cetyl Alcohol | 0.60 | 0.60 | 0.60 | 0.60 | 0.60 |
| Lauryl Alcohol | | | 0.35 | 0.35 | 0.35 |
| Dihydrogenated Tallowamidoethyl Hydroxyethylmonium Methosulfate[17] | 0.15 | 0.15 | 0.15 | 0.15 | 0.15 |
| 1-Propanaminium, N,N,N-trimethyl-3-[(2-methyl-1-oxo-2-propenyl)amino]-, chloride; (Poly(Methacrylamidopropyl trimethyl ammonium chloride))[1,2] | | | | | |
| Methacryloamidopropyl-pentamethyl-1,3-propylene-2-ol-ammonium dichloride[3] | 0.40 | | | | |
| N,N,N,N',N',N'',N''-heptamethyl-N''-3-(1-oxo-2-methyl-2-propenyl)aminopropyl-9-oxo-8-azo-decane-1,4,10-triammonium trichloride (18) | | 0.40 | | | |
| 1-Propanaminium, N,N,N-trimethyl-3-[(1-oxo-2-propenyl)amino]-, chloride; (Poly(Acrylamidopropyl trimethyl ammonium chloride))[4] | | | 0.40 | | |
| [3-methacryloylamino)propyl] dimethylethylammonium ethylsulfate homopolymer[5] | | | | 0.40 | |
| [(2-methacryloyloxy)ethyl]trimethylammonium methylsulfate homopolymer[6] | | | | | 0.40 |
| Ethylene Glycol Distearate | 1.50 | 1.50 | 1.50 | 1.50 | 1.50 |
| Trihydroxystearin[7] | | | | | |
| Polyethylene Glycol (14000)[8] | 0.17 | 0.17 | 0.17 | 0.17 | 0.17 |
| Fragrance | 0.55 | 0.55 | 0.55 | 0.55 | 0.55 |

-continued

| Hompolymers | | | | | |
|---|---|---|---|---|---|
| Sodium Chloride | 0.80 | 0.80 | 0.80 | 0.80 | 0.80 |
| Ammonium Xylenesulfonate | | | | | |
| Citric Acid | 0.04 | 0.04 | 0.04 | 0.04 | 0.04 |
| Sodium Citrate | 0.40 | 0.40 | 0.40 | 0.40 | 0.40 |
| Sodium Benzoate | 0.25 | 0.25 | 0.25 | 0.25 | 0.25 |
| Ethylene Diamine Tetra Acetic Acid | 0.10 | 0.10 | 0.10 | 0.10 | 0.10 |
| Dimethicone[9,10,11] | 0.80 [9] | 0.80 [9] | 0.50 [9] | 0.50 [9] | |
| Polydecene[12] | | | | | |
| Trimethylolpropane Tricaprylate/Tricaprate[13] | | | | | |
| Water and Minors (QS to 100%) | | | | | |

[1] HMW MAPTAC (Rhodia) [charge density = 4.5 meq/g, molecular weight ~860,000]
[2] HHMW MAPTAC (Rhodia) [charge density = 4.5 meq/g, molecular weight ~1,500,000]
[3] Diquat (Rhodia) [charge density = 5.60 meq/g, molecular weight ~252,000]
[4] APTAC (Rhodia) [charge density = 4.88 meq/g, molecular weight ~1,916,000]
[5] Homopolymer of DMAPMA + DES (Rhodia) [charge density = 3.09 meq/g, molecular weight ~180,000]
[6] Homopolymer of METAMS (Rhodia) [charge density = 3.53 meq/g, molecular weight ~313,000]
[7] Thixcin R (Rheox)
[8] PEG 14M (Dow Chemical)
[9] Viscasil 330M (General Electric Silicones)
[10] Dow Corning ® 1664 Emulsion (Dow Corning)
[11] Dow Corning ® 2-1865 Microemulsion (Dow Corning)
[12] Puresyn 6, MCP-1812 (Mobil)
[13] Mobil P43 (Mobil)
[14] Miranol Ultra L32 (Rhodia)
[15] MACKAM 151C (McIntyre)
[16] Tegobetaine F-B (Goldschmidt)
[17] Varisoft 110 (Witco)
(18) Triqaut (Rhodia) [charge density = 6.07]

| | Copolymers | | | | |
|---|---|---|---|---|---|
| | EXAMPLE COMPOSITION | | | | |
| | 11 | 12 | 13 | 14 | 15 |
| Ammonium Laureth Sulfate (AE$_3$S) | 10.00 | 10.00 | | | |
| Ammonium Lauryl Sulfate (ALS) | 6.00 | 6.00 | | | |
| Sodium Laureth Sulfate (SE$_3$S) | | | 6.50 | 6.50 | 6.50 |
| Sodium Lauryl Sulfate (SLS) | | | 5.50 | 5.50 | 5.50 |
| Sodium Lauroamphoacetate[15] | | | | | |
| Cocaminopropionic Acid[16] | | | | | |
| Cocamidopropyl Betaine[17] | | | | | |
| Cocamide MEA | 0.80 | 0.80 | 0.80 | 0.80 | 0.80 |
| Cetyl Alcohol | 0.90 | 0.90 | 0.60 | 0.60 | 0.60 |
| Lauryl Alcohol | | | 0.35 | 0.35 | 0.35 |
| Dihydrogenated Tallowamidoethyl Hydroxyethylmonium Methosulfate[18] | | | 0.15 | 0.15 | 0.15 |
| Trimethylammoniopropylmethacrylamide chloride-N-Hydroxyethyl acrylate copolymer[1,2,3] | 1.00 [1] | 0.50 [2] | 0.40 [3] | 0.05 [2] | 0.40 [2] |
| Trimethylammoniopropylmethacrylamide chloride-N-vinylpyrrolidone copolymer[4,5] | | | | | |
| Dimethyldiallyl ammonium chloride-N-b-Hydroxyethyl acrylate copolymer[6] | | | | | |
| Trimethylammoniopropylmethacrylamide chloride-N-Methacrylamidopropyldimethylammonium methylcarboxylate copolymer[7] | | | | | |
| Ethylene Glycol Distearate | 1.50 | 1.50 | | 1.50 | 1.50 |
| Trihydroxystearin[8] | | | 0.25 | | |
| Polyethylene Glycol (14000)[9] | | | 0.17 | 0.17 | 0.17 |
| Fragrance | 0.55 | 0.70 | 0.55 | 0.55 | 0.55 |
| Sodium Chloride | 1.00 | 1.30 | 0.80 | 0.80 | 0.80 |
| Ammonium Xylenesulfonate | | | | | |
| Citric Acid | 0.04 | 0.04 | 0.04 | 0.04 | 0.04 |
| Sodium Citrate | 0.40 | 0.40 | 0.40 | 0.40 | 0.40 |
| Sodium Benzoate | 0.25 | 0.25 | 0.25 | 0.25 | 0.25 |
| Ethylene Diamine Tetra Acetic Acid | 0.10 | 0.10 | 0.10 | 0.10 | 0.10 |
| Dimethicone[10,11,12] | 1.35 [10] | 1.00 [10] | | 0.50 [10] | 0.50 [10] |
| Polydecene[13] | 0.40 | 0.40 | | | |
| Trimethylolpropane Tricaprylate/Tricaprate[14] | 0.10 | 0.10 | | | |
| Water and Minors (QS to 100%) | | | | | |

-continued

Copolymers

| | EXAMPLE COMPOSITION | | | |
|---|---|---|---|---|
| | 16 | 17 | 18 | 19 |
| Ammonium Laureth Sulfate (AE$_3$S) | | | | |
| Ammonium Lauryl Sulfate (ALS) | | | | |
| Sodium Laureth Sulfate (SE$_3$S) | 6.50 | 6.50 | 6.50 | 6.50 |
| Sodium Lauryl Sulfate (SLS) | 5.50 | 5.50 | 5.50 | 5.50 |
| Sodium Lauroamphoacetate[15] | | | | 2.00 |
| Cocaminopropionic Acid[16] | | | 1.00 | |
| Cocamidopropyl Betaine[17] | | | 1.00 | |
| Cocamide MEA | 0.80 | 0.80 | 0.80 | 0.80 |
| Cetyl Alcohol | 0.60 | 0.60 | 0.60 | 0.60 |
| Lauryl Alcohol | 0.35 | 0.35 | 0.35 | 0.35 |
| Dihydrogenated Tallowamidoethyl Hydroxyethylmonium Methosulfate[18] | 0.15 | 0.15 | 0.15 | 0.15 |
| Trimethylammoniopropylmethacrylamide chloride-N-Hydroxyethyl acrylate copolymer[1,2,3] | | | | |
| Trimethylammoniopropylmethacrylamide chloride-N-vinylpyrrolidone copolymer[4,5] | 0.40 [4] | 0.40 [5] | | |
| Dimethyldiallyl ammonium chloride-N-b-Hydroxyethyl acrylate copolymer[6] | | | 0.40 | |
| Trimethylammoniopropylmethacrylamide chloride-N-Methacrylamidopropyldimethylammonium methylcarboxylate copolymer[7] | | | | 0.40 |
| Ethylene Glycol Distearate | 1.50 | 1.50 | 1.50 | 1.50 |
| Trihydroxystearin[8] | | | | |
| Polyethylene Glycol (14000)[9] | 0.17 | 0.17 | 0.17 | 0.17 |
| Fragrance | 0.55 | 0.55 | 0.55 | 0.55 |
| Sodium Chloride | 0.80 | 0.80 | 0.80 | 0.80 |
| Ammonium Xylenesulfonate | | | | |
| Citric Acid | 0.04 | 0.04 | 0.04 | 0.04 |
| Sodium Citrate | 0.40 | 0.40 | 0.40 | 0.40 |
| Sodium Benzoate | 0.25 | 0.25 | 0.25 | 0.25 |
| Ethylene Diamine Tetra Acetic Acid | 0.10 | 0.10 | 0.10 | 0.10 |
| Dimethicone[10,11,12] | 0.50 [10] | 0.50 [10] | 2.00 [11] | 2.00 [12] |
| Polydecene[13] | | | | |
| Trimethylolpropane Tricaprylate/Tricaprate[14] | | | | |
| Water and Minors (QS to 100%) | | | | |

[1]1:9 HEA:MAPTAC (Rhodia) [charge density = 4.29 meq/g, molecular weight ~276,000]
[2]3:7 HEA:MAPTAC (Rhodia) [charge density = 3.71 meq/g, molecular weight ~648,000]
[3]3:7 HEA:MAPTAC (Rhodia) [charge density = 3.71 meq/g, molecular weight ~1,200,000]
[4]1:9 VP:MAPTAC (Rhodia) [charge density = 4.30 meq/g, molecular weight ~242,000]
[5]3:7 VP:MAPTAC (Rhodia) [charge density = 3.74 meq/g, molecular weight ~503,000]
[6]1:9 HEA:DMDAAC (Rhodia) [charge density = 5.75 meq/g, molecular weight ~274,000]
[7]1:1 AP:MAPTAC (Rhodia) [charge density = 3.95 meq/g, molecular weight ~243,000]
[8]Thixcin R (Rheox)
[9]PEG 14M (Dow Chemical)
[10]Viscasil 330M (General Electric Silicones)
[11]Dow Corning ® 1664 Emulsion (Dow Corning)
[12]Dow Corning ® 2-1865 Microemulsion (Dow Corning)
[13]Puresyn 6, MCP-1812 (Mobil)
[14]Mobil P43 (Mobil)
[15]Miranol Ultra L32 (Rhodia)
[16]MACKAM 151C (McIntyre)
[17]Tegobetaine F-B (Goldschmidt)
[18]Varisoft 110 (Witco)

What is claimed is:

1. A personal cleansing composition comprising:
   A. from about 5% to about 50% by weight of a detersive surfactant component selected from the group consisting of anionic surfactants, amphoteric and zwitterionic surfactants having an attached group that is anionic at the pH of the composition, and combinations thereof;
   B. from about 0.025% to about 5% by weight of a water soluble or dispersible, cationic, non-crosslinked, conditioning polymer mixture comprising:
      (a) a copolymer comprising:
         ii. one or more cationic monomer units selected from the group consisting of diallyldimethyl ammonium chloride and 1-Propanaminium, N,N,N-trimethyl-3-[(2-methyl-1-oxo-2-propenyl)amino]-, chloride, and
         iii. one or more nonionic; the nonionic units being selected from the group consisting of vinyl nitriles, vinylamine amides, vinyl alcohol, vinyl pyrolidone, vinyl aromatic compounds, styrene, acrylonitrile, methylacrylate, ethylacrylate, n-propylacrylate, n-butylacrylate, methylmethacrylate, ethylmethacrylate, n-propylmethacrylate, n-butylmethacrylate, 2-ethyl-hexyl acrylate, 2-ethylhexyl methacrylate, 2-hydroxyethylacrylate and 2-hydroxyethylmethacrylate;

wherein said copolymer has a positive charge, a cationic charge density of from about 2 meq/gm to about 10 meq/gm, and an average molecular weight of from 100,000 to 2,000,000; and (b) a homopolymer having a cationic charge density of from about 5 meq/gm to about 10 meq/gm, the homopolymer being selected from the group consisting of: diallyldimethyl ammonium chloride and 1-Propanaminium, N,N,N-trimethyl-3-[(2-methyl-1-oxo-2-propenyl)amino]-, chloride; and C. from about 20% to about 94% by weight of water;

wherein said composition comprises lyotropic liquid crystals.

2. The personal cleansing composition of claim 1 further comprising from about 0.05% to about 5% by weight of dispersed droplets of a water insoluble hair conditioning agent having a volume average droplet diameter of from about 5 microns to about 125 microns.

3. The personal cleansing composition of claim 1 wherein the cationic charge density of the cationic polymer is from about 3 meq/gm to about 8 meq/gm.

4. The personal cleansing composition of claim 1 further comprising from about 0.1% to about 5%, by weight, of a phase separation initiator selected from the group consisting of electrolytes, amphiphiles and mixtures thereof.

5. The composition of claim 1 wherein said cationic homopolymer promotes the formation of a microscopic-phase separation of lyotropic liquid crystals in said composition; the liquid crystals exhibiting birefringence.

6. A method of treating hair by administering a safe and effective amount of the composition according to claim 1.

7. The composition of claim 1 wherein the cationic, non-crosslinked, conditioning polymer mixture is selected as a copolymer consisting of diallyldimethyl ammonium chloride and 2-hydroxyethylacrylate and a homopolymer selected from the group consisting of diallyldimethyl ammonium chloride and 1-Propanaminium, N,N,N-trimethyl-3-[(2-methyl-1-oxo-2-propenyl)amino]-, chloride.

8. The composition of claim 1 wherein the cationic, non-crosslinked, conditioning polymer mixture is selected as a copolymer consisting of 1-Propanaminium, N,N,N-trimethyl-3-[(2-methyl-1-oxo-2-propenyl)amino]-, chloride and 2-hydroxyethylacrylate and a homopolymer selected from the group consisting of diallyldimethyl ammonium chloride and 1-Propanaminium, N,N,N-trimethyl-3-[(2-methyl-1-oxo-2-propenyl)amino]-, chloride.

9. The composition of claim 1 wherein the cationic, non-crosslinked, conditioning polymer mixture is selected as a copolymer consisting of 1-Propanaminium, N,N,N-trimethyl-3-[(2-methyl-1-oxo-2-propenyl)amino]-, chloride and vinyl pyrolidone and a homopolymer selected from the group consisting of diallyldimethyl ammonium chloride and 1-Propanaminium, N,N,N-trimethyl-3-[(2-methyl-1-oxo-2-propenyl)amino]-, chloride.

* * * * *